United States Patent
Gatti-Lafranconi et al.

(10) Patent No.: US 11,767,558 B2
(45) Date of Patent: Sep. 26, 2023

(54) ADDING NUCLEOTIDES DURING SEQUENCE DETECTION

(71) Applicant: Illumina Cambridge Limited, Cambridge (GB)

(72) Inventors: Pietro Gatti-Lafranconi, Cambridge (GB); Philip Balding, Cambridge (GB)

(73) Assignee: Illumina Cambridge Limited, Cambridge (GB)

( * ) Notice: Subject to any disclaimer, the term of this patent is extended or adjusted under 35 U.S.C. 154(b) by 766 days.

(21) Appl. No.: 16/704,345

(22) Filed: Dec. 5, 2019

(65) Prior Publication Data

US 2020/0190576 A1    Jun. 18, 2020

Related U.S. Application Data

(60) Provisional application No. 62/779,609, filed on Dec. 14, 2018.

(51) Int. Cl.
*C12Q 1/6874* (2018.01)
*B01L 3/00* (2006.01)
*C12Q 1/25* (2006.01)

(52) U.S. Cl.
CPC ...... *C12Q 1/6874* (2013.01); *B01L 3/502761* (2013.01); *C12Q 1/25* (2013.01); *C12Q 2527/146* (2013.01); *C12Q 2535/00* (2013.01); *C12Q 2537/149* (2013.01)

(58) Field of Classification Search
None
See application file for complete search history.

(56) References Cited

U.S. PATENT DOCUMENTS

| | | | |
|---|---|---|---|
| 7,883,869 B2 | 2/2011 | Ju et al. | |
| 8,772,473 B2 | 7/2014 | Huang et al. | |
| 2013/0137091 A1 | 5/2013 | Gordon et al. | |
| 2014/0080795 A1* | 3/2014 | Rahman | A61K 31/05 435/375 |
| 2015/0080232 A1 | 3/2015 | Ju et al. | |
| 2016/0032377 A1* | 2/2016 | Chen et al. | C12N 9/1252 506/26 |
| 2016/0040225 A1* | 2/2016 | Wu et al. | C12Q 1/6869 435/6.1 |
| 2018/0044715 A1 | 2/2018 | Iyidogan et al. | |

FOREIGN PATENT DOCUMENTS

| | | | | |
|---|---|---|---|---|
| WO | 2006064199 A1 | 6/2006 | | |
| WO | WO-2006064199 A1 * | 6/2006 | ........... | C12Q 1/6816 |
| WO | 2018165207 A1 | 9/2018 | | |
| WO | WO-2018165207 A1 * | 9/2018 | ............. | C07H 21/04 |

OTHER PUBLICATIONS

Guo, et al., "An Integrated System for DNA Sequencing by Synthesis Using Novel Nucleotide Analogues", Accounts of Chemical Research, Apr. 20, 2010, 551-563.

* cited by examiner

*Primary Examiner* — Kaijiang Zhang
(74) *Attorney, Agent, or Firm* — Mueting Raasch Group

(57) ABSTRACT

Polynucleotide sequencing methods include incubating unlabeled nucleotides with a cluster of template polynucleotide strands having the same sequence when the identity of the previously added labeled nucleotide is being detected. The detection step provides time for the addition of the unlabeled nucleotides to be incorporated into the copy strands in which the previously added labeled nucleotide did not get incorporated. Thus, at the end of the detection step, all or most of the copy strands will be in phase and ready to incorporate the appropriate labeled nucleotide in the subsequence incorporate step.

17 Claims, 7 Drawing Sheets
Specification includes a Sequence Listing.

ADDING NUCLEOTIDES DURING SEQUENCE DETECTION

PRIORITY

This application claims the benefit of U.S. Provisional Application No. 62/779,609, filed Dec. 14, 2018, the disclosure of which is incorporated by reference herein in its entirety.

SEQUENCE LISTING

This application contains a Sequence Listing electronically submitted to the United States Patent and Trademark Office via Patent Center as an XML file entitled "531.001549US01" having a size of 2.61 kilobytes and created on 10 Apr. 2023. Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein. No new matter has been added.

FIELD

The present disclosure relates to, among other things, sequencing of polynucleotides.

BACKGROUND

Sequencing of a template polynucleotide strand may occur through multiple cycles of reactions by which one detectable nucleotide per cycle is incorporated into a copy strand. The detectable nucleotides are typically blocked to prevent incorporation of more than one detectable nucleotide per cycle. After an incubation time, a wash step is typically performed to remove any unincorporated detectable nucleotide. A detection step, in which the identity of the detectable nucleotide incorporated into the copy strand is determined, may then be performed. Next, an unblocking step and cleavage or masking step is performed in which the blocking agent is removed from the last incorporated nucleotide in the copy strand and the detectable moiety is cleaved from or masked on the last nucleotide incorporated into the copy strand. In some instances, the detectable moiety serves as the blocking agent, and removal of the detectable moiety may remove the blocking agent. The cycle is then repeated by introducing detectable nucleotides in an incorporation step.

In many cases, clusters of template polynucleotide strands having the same sequence are simultaneously sequenced. The clusters serve to amplify the signal produced by detectable nucleotides incorporated into the copy strands. Because the clusters contain multiple template strands of the same sequence, the nucleotide incorporated into the corresponding copy strands at each round of nucleotide addition should be the same, and the signal from the detectable nucleotide should be enhanced proportional to the number of copies of the template strand in the cluster.

A recent goal of sequencing of polynucleotides is to decrease the time to complete the sequencing while maintaining high fidelity. One way to achieve decreased sequencing time is to reduce the cycle time by shortening the duration of the incorporation step. A number of more efficient polymerases and modified nucleotides have been developed to provide more efficient incorporation of nucleotides into the copy strand. However, the incorporation step still tends to suffer from incomplete incorporation of nucleotides across all template strands being sequenced.

When, during an incorporation step, a nucleotide is not incorporated into a copy strand in a cluster containing multiple template strands having the same sequence, the copy strand in which the nucleotide is not incorporated is said to be out of phase with those copy strands in which the nucleotide is incorporated during the incorporation step. As the number of copy strands that are out of phase increases with further cycles, the signal from a cluster may become too heterogeneous to determine the nucleotide that was incorporated into the in-phase copy strands.

SUMMARY

The present disclosure describes, among other things, polynucleotide sequencing methods that allow for short cycle times for incorporation of labeled nucleotides while reducing phasing. The methods include incubating unlabeled nucleotides with a cluster of template polynucleotide strands having the same sequence when the identity of the previously added labeled nucleotide is being detected. The detection step provides time for the addition of the unlabeled nucleotides to be incorporated into the copy strands in which the previously added labeled nucleotide did not get incorporated. Thus, at the end of the detection step, all or most of the copy strands will be in phase and ready to incorporate the appropriate labeled nucleotide in the subsequent incorporate step.

In some embodiments, the polynucleotide sequencing method comprises introducing a chain extending enzyme and a mixture of blocked, labeled nucleotides to a flow cell comprising a site at which multiple template polynucleotide strands having the same nucleotide sequence are bound to a surface of the flow cell. The chain extending enzyme is configured to incorporate an appropriate one of the blocked, labeled nucleotides into copy polynucleotide strands, based on the sequence of the template strands to which the copy polynucleotide strands correspond. The method further comprises washing unincorporated blocked, labeled nucleotides away from the flow cell and introducing a composition comprising a mixture of blocked, unlabeled nucleotides to the flow cell during or after the washing away of the unincorporated blocked, labeled nucleotides from the flow cell. A blocked, unlabeled nucleotide of the mixture of the blocked, unlabeled nucleotides is available for incorporation into the copy polynucleotide strands, based on a sequence of the template strands to which the copy polynucleotide strands correspond, provided that the previously incorporated nucleotide in the copy strand, if any, is not blocked. The method also comprises detecting the identity of the one blocked, labeled nucleotide incorporated into the copy strands, if any, while the mixture of blocked, unlabeled nucleotides is incubated with the flow cell.

The label and block may then be removed from the blocked, labeled nucleotide incorporated into the copy strands and the block may be removed from the blocked, unlabeled nucleotide, if any, incorporated into the copy strands. The process may then be repeated for a predetermined number of cycles or until the sequencing is complete.

The details of one or more embodiments are set forth in the accompanying drawings and the description below. Other features, objects, and advantages will be apparent from the description and drawings, and from the claims.

It is to be understood that both the foregoing general description and the following detailed description present embodiments of the subject matter of the present disclosure and are intended to provide an overview or framework for understanding the nature and character of the subject matter of the present disclosure as it is claimed. The accompanying drawings are included to provide a further understanding of the subject matter of the present disclosure and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative and are not intended to limit the scope of the claims in any manner.

DESCRIPTION OF DRAWINGS

The following detailed description of specific embodiments of the present disclosure may be best understood when read in conjunction with the following drawings.

Figures 1, 2:
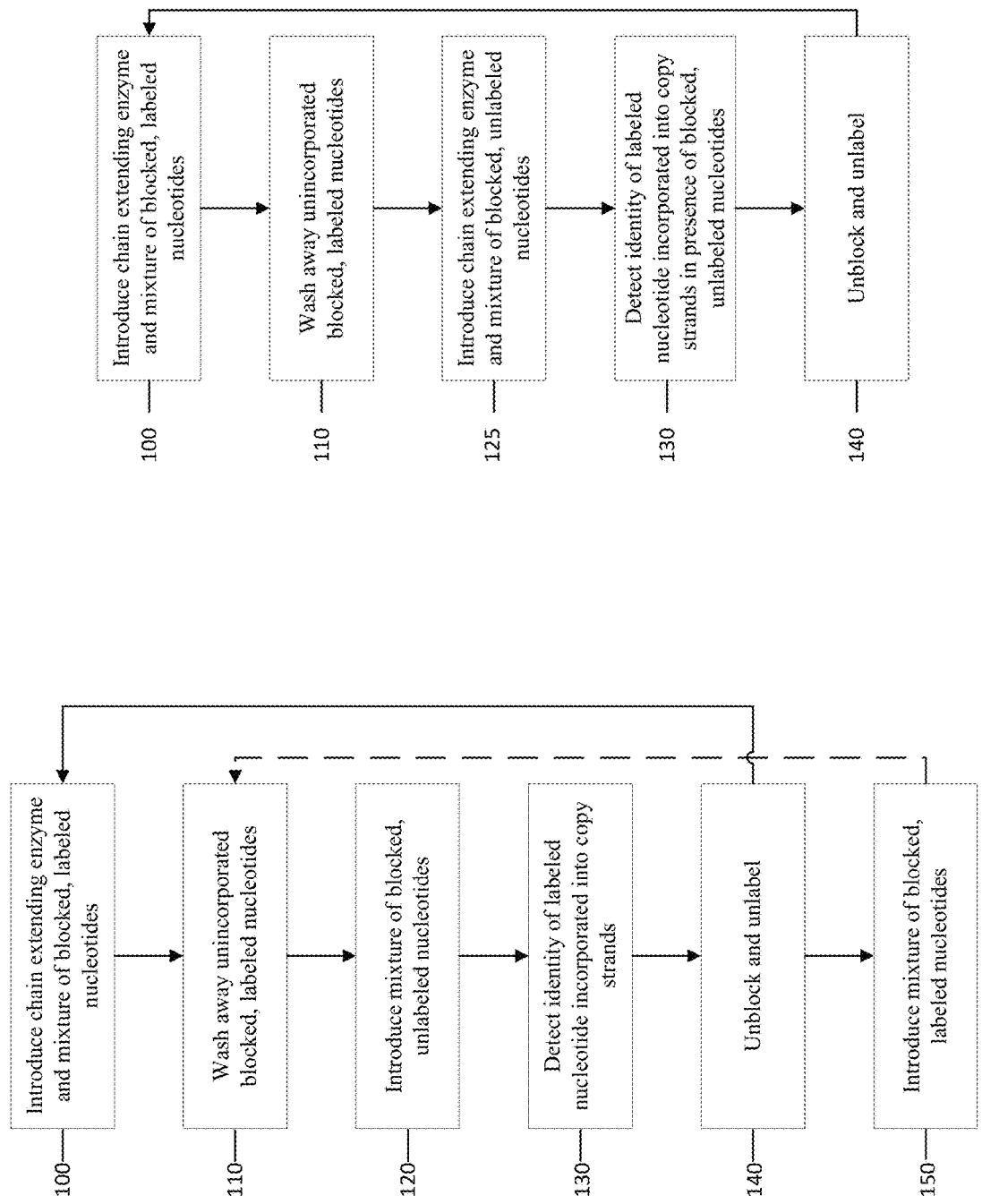
FIGS. 1-2 are flow diagrams illustrating embodiments of sequences methods described herein.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

DETAILED DESCRIPTION

Reference will now be made in greater detail to various embodiments of the subject matter of the present disclosure, some embodiments of which are illustrated in the accompanying drawings.

All scientific and technical terms used herein have meanings commonly used in the art unless otherwise specified. The definitions provided herein are to facilitate understanding of certain terms used frequently herein and are not meant to limit the scope of the present disclosure.

As used herein, singular forms "a," "an" and "the" include plural referents unless the context clearly dictates otherwise. Thus, for example, reference to a "template polynucleotide sequence" includes examples having two or more such "template polynucleotide sequences" unless the context clearly indicates otherwise.

As used in this specification and the appended claims, the term "or" is generally employed in its sense including "and/or" unless the content clearly dictates otherwise. The term "and/or" means one or all of the listed elements or a combination of any two or more of the listed elements. The use of "and/or" in some instances does not imply that the use of "or" in other instances may not mean "and/or."

As used herein, "have", "has", "having", "include", "includes", "including", "comprise", "comprises", "comprising" or the like are used in their open-ended inclusive sense, and generally mean "include, but not limited to", "includes, but not limited to", or "including, but not limited to".

"Optional" or "optionally" means that the subsequently described event, circumstance, or component, can or cannot occur, and that the description includes instances where the event, circumstance, or component, occurs and instances where it does not.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the inventive technology.

In addition, the recitations herein of numerical ranges by endpoints include all numbers subsumed within that range (e.g., 1 to 5 includes 1, 1.5, 2, 2.75, 3, 3.80, 4, 5, etc.). Where a range of values is "greater than", "less than", etc. a particular value, that value is included within the range.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. However, it will be understood that a presented order is one embodiment of an order by which the method may carried out. Any recited single or multiple feature or aspect in any one claim may be combined or permuted with any other recited feature or aspect in any other claim or claims.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a method comprising an incorporation step, a detection step, a deprotection step, and one or more wash steps includes embodiments where the method consists of enumerated steps and embodiments where the method consists essentially of the enumerated.

As used herein, "providing" in the context of a compound, composition, or article means making the compound, composition, or article, purchasing the compound, composition or article, or otherwise obtaining the compound, composition or article.

As used herein, the term "chain extending enzyme" is an enzyme that produces a copy replicate of a polynucleotide using the polynucleotide as a template strand. For example, the chain extending enzyme may be an enzyme having polymerase activity. Typically, DNA polymerases bind to the template strand and then move down the template strand sequentially adding nucleotides to the free hydroxyl group at the 3' end of a growing strand of nucleic acid. DNA polymerases typically synthesize complementary DNA molecules from DNA templates and RNA polymerases typically synthesize RNA molecules from DNA templates (transcription). Polymerases may use a short RNA or DNA strand, called a primer, to begin strand growth. Some polymerases may displace the strand upstream of the site where they are adding bases to a chain. Such polymerases are said to be strand displacing, meaning they have an activity that removes a complementary strand from a template strand being read by the polymerase. Exemplary polymerases having strand displacing activity include, without limitation, the large fragment of Bst (*Bacillus stearothermophilus*) polymerase, exo-Klenow polymerase or sequencing grade T7 exo-polymerase. Some polymerases degrade the strand in front of them, effectively replacing it with the growing chain behind (5' exonuclease activity). Some polymerases have an activity that degrades the strand behind them (3' exonuclease activity). Some useful polymerases have been modified, either by mutation or otherwise, to reduce or eliminate 3' and/or 5' exonuclease activity.

As used herein, the term "primer" and its derivatives refer generally to any polynucleotide that may hybridize to a target sequence of interest. Typically, the primer functions as a substrate onto which nucleotides may be polymerized by a polymerase; in some embodiments, however, the primer may become incorporated into the synthesized polynucleotide strand and provide a site to which another primer may hybridize to prime synthesis of a new strand that is complementary to the synthesized nucleic acid molecule. The primer may be comprised of any combination of nucleotides or analogs thereof. In some embodiments, the primer is a single-stranded oligonucleotide or polynucleotide.

The terms "polynucleotide" and "oligonucleotide" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). As used herein, "amplified target sequences" and its derivatives, refers generally to a polynucleotide sequence produced by the amplifying the target sequences using target-specific primers and the methods provided herein. The amplified target sequences may be either of the same sense (i.e the positive strand) or antisense (i.e., the negative strand) with respect to the target sequences.

Suitable nucleotides for use in the provided methods include, but are not limited to, deoxynucleotide triphosphates, deoxyadenosine triphosphate (dATP), deoxythymidine triphosphate (dTTP), deoxycytidine triphosphate (dCTP), and deoxyguanosine triphosphate (dGTP). Optionally, the nucleotides used in the provided methods, whether labeled or unlabeled, can include a blocking moiety such as a reversible terminator moiety that inhibits chain extension. Suitable labels for use on the labeled nucleotides include, but are not limited to, haptens, radionucleotides, enzymes, fluorescent labels, chemiluminescent labels, and chromogenic agents.

A polynucleotide will generally contain phosphodiester bonds, although in some cases nucleic acid analogs can have alternate backbones, comprising, for example, phosphoramide (Beaucage et al., Tetrahedron 49(10): 1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114: 1895 (1992); Meier et al., Chem. Int. Ed. Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Polynucleotides containing one or more carbocyclic sugars are also included within the definition of polynucleotides (see Jenkins et al., Chem. Soc. Rev. (1995) pp 169-176). Several polynucleotide analogs are described in Rawls, C & E News Jun. 2, 1997 page 35. All these references are hereby expressly incorporated by reference. These modifications of the ribose-phosphate backbone may be done to facilitate the addition of labels, or to increase the stability and half-life of such molecules in physiological environments.

A polynucleotide will generally contain a specific sequence of four nucleotide bases: adenine (A); cytosine (C); guanine (G); and thymine (T). Uracil (U) can also be present, for example, as a natural replacement for thymine when the nucleic acid is RNA. Uracil can also be used in DNA. A polynucleotide may also include native or non-native bases. In this regard, a native deoxyribonucleic acid polynucleotide may have one or more bases selected from the group consisting of adenine, thymine, cytosine or guanine and a ribonucleic acid may have one or more bases selected from the group consisting of uracil, adenine, cytosine or guanine. It will be understood that a deoxyribonucleic acid polynucleotides used in the methods or compositions set forth herein may include, for example, uracil bases and a ribonucleic acid can include, for example, a thymine base. Exemplary non-native bases that may be included in a nucleic acid, whether having a native backbone or analog structure, include, without limitation, inosine, xathanine, hypoxathanine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thioLiracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. Optionally, isocytosine and isoguanine may be included in a nucleic acid in order to reduce non-specific hybridization, as generally described in U.S. Pat. No. 5,681,702, which is incorporated by reference herein in its entirety.

A non-native base used in a polynucleotide may have universal base pairing activity such that it is capable of base pairing with any other naturally occurring base. Exemplary bases having universal base pairing activity include 3-nitropyrrole and 5-nitroindole. Other bases that can be used include those that have base pairing activity with a subset of the naturally occurring bases such as inosine, which base-pairs with cytosine, adenine or uracil.

Incorporation of a nucleotide into a polynucleotide strand refers to joining of the nucleotide to a free 3 ' hydroxyl group of the polynucleotide strand via formation of a phosphodiester linkage with the 5' phosphate group of the nucleotide. The polynucleotide template to be sequenced can be DNA or RNA, or even a hybrid molecule that includes both deoxynucleotides and ribonucleotides. The polynucleotide can include naturally occurring and/or non-naturally occurring nucleotides and natural or non-natural backbone linkages.

The present disclosure describes, among other things, polynucleotide sequencing methods that allow for short cycle times for incorporation of labeled nucleotides while reducing phasing. The methods include incubating unlabeled nucleotides with a cluster of template polynucleotide strands having the same sequence when the identity of the previously added labeled nucleotide is being detected. The detection step provides time for the addition of the unlabeled nucleotides to be incorporated into the copy strands in which the previously labeled nucleotide from the previous incorporation step did not get incorporated. Thus, at the end of the detection step, all or most of the copy strands will be in phase and ready to incorporate the appropriate labeled nucleotide in the subsequence incorporate step.

The detection step tends to take substantially more time than the incorporation step, particularly if the detection step includes imaging. Accordingly, the detection step may provide substantially more time for nucleotide incorporation than the incorporation step, which may substantially reduce phasing due to lagging. Because the nucleotides incorporated into the lagging copy strands are unlabeled, they do not produce a signal during detection and thus do not interfere with detection.

As discussed throughout, provided are improved methods for sequencing polynucleotides. Exemplary sequencing methods are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference. One useful method for high throughput or rapid sequencing is sequencing by synthesis (SBS). SBS techniques include, but are not limited to, the Genome Analyzer systems (Illumina Inc., San Diego, Calif.) and the True Single Molecule Sequencing (tSMS)™ systems (Helicos BioSciences Corporation, Cambridge, Mass.). Briefly, a number of sequencing by synthesis reactions are used to elucidate the identity of a plurality of bases at target positions within a target sequence. All of these reactions rely on the use of a target nucleic acid sequence having at least two domains; a first domain to which a sequencing primer will hybridize, and an adjacent second domain, for which sequence information is desired. Upon formation of an assay complex, extension enzymes are used to add deoxynucleotide triphosphates (dNTPs) to a sequencing primer that is hybridized to first domain, and each addition of dNTPs is read to determine the identity of the added dNTP. This may proceed for many cycles. SBS techniques such as, the Genome Analyzer systems (Illumina Inc., San Diego, Calif.) and the True Single Molecule Sequencing (tSMS)™ systems (Helicos BioSciences Corporation, Cambridge, Mass.), utilize labeled nucleotides to determine the sequence of a target nucleic acid molecule. A target nucleic acid molecule can be hybridized with a primer and incubated in the presence of a polymerase and a labeled nucleotide containing a blocking group. The primer is extended such that the nucleotide is incorporated. The presence of the blocking group permits only one round of incorporation, that is, the incorporation of a single nucleotide. The presence of the label permits identification of the incorporated nucleotide. A plurality of homogenous single nucleotide bases can be added during each cycle, such as used in the True Single Molecule Sequencing (tSMS)™ systems (Helicos BioSciences Corporation, Cambridge, Mass.) or, alternatively, all four nucleotide bases can be added during each cycle simultaneously, such as used in the Genome Analyzer systems (Illumina Inc., San Diego, Calif.), particularly when each base is associated with a distinguishable label. After identifying the incorporated nucleotide by its corresponding label, both the label and the blocking group can be removed, thereby allowing a subsequent round of incorporation and identification. Determining the identity of the added nucleotide base includes, in some embodiments, repeated exposure of the newly added labeled bases a light source that can induce a detectable emission due the addition of a specific nucleotide base, i.e. dATP, dCTP, dGTP or dTTP. The methods and compositions disclosed herein are particularly useful for such SBS techniques. In addition, the methods and compositions described herein may be particularly useful for sequencing from an array of nucleic acids, where multiple sequences can be read simultaneously from multiple positions on the array since each nucleotide at each position can be identified based on its identifiable label. Exemplary methods are described in US 2009/0088327; US 2010/0028885; and US 2009/0325172, each of which is incorporated herein by reference.

Referring now to FIGS. 1-2, overviews of embodiments of sequencing methods are shown. The methods include introducing a first chain extending enzyme and a mixture of blocked, labeled nucleotides to a site comprising multiple template polynucleotide strands having the same nucleotide sequence (100). The first chain extending enzyme is configured to incorporate an appropriate one of the blocked, labeled nucleotides into copy polynucleotide strands, based on the sequence of the template strands to which the copy polynucleotide strands correspond. During or prior to the first round of incorporation of nucleotides, a polynucleotide primer may be hybridized to the template strand to facilitate sequencing from a predetermined starting position.

The blocked, labeled nucleotides are incubated with the template strands and chain extending enzyme for a period of time in an "incorporation step." The incorporation step may take any suitable amount of time. As the time of the incorporation step increases, phasing tends to decrease because sufficient time is provided for incorporation of a blocked, labeled nucleotide into a copy strand. However, longer incorporation steps prevent the common goal of faster sequencing.

While many current sequencing methods provide for an incorporation step time sufficiently long to reduce phasing to a sufficiently low level to provide an acceptable error rate over the number of cycles in a run, the present methods may, in some embodiments, accommodate a higher level of phasing during the incorporation step because correction of phasing may occur during the detection step.

One advantage of the methods described herein is that the time of the incorporation step may be reduced to a level that results in a previously unacceptable level of phasing because lagging copy strands may be brought back into phase during a detection step. By reducing the time of the incorporation step, the time of the overall sequencing process may be reduced.

In some embodiments, the time that a composition comprising a mixture of blocked, labeled nucleotides is incubated with the template polynucleotides is between 1 second and 60 seconds, such as from 5 seconds to 45 sections, or from 10 seconds to 30 seconds. In some embodiments, the time that a composition comprising a mixture of blocked, labeled nucleotides with the template polynucleotides is 15 seconds or less, such as 10 seconds or less, or 7.5 seconds or less.

Preferably, the incorporation step is sufficiently long to allow for incorporation of blocked, labeled nucleotide in a sufficient number of copy strands to produce a detectable signal during a detection step.

Still with reference to FIGS. 1-2, after incubating the blocked, labeled nucleotides with the template strands and chain extending enzyme in the incorporation step, the unincorporated blocked, labeled nucleotides may be washed away from the site (110), and a composition comprising a mixture of blocked, unlabeled nucleotides may be introduced to the site comprising the multiple template polynucleotide strands (120). In some embodiments, the introduction of the composition comprising the mixture of blocked, unlabeled nucleotides (step 120) serves to wash away the unincorporated blocked, labeled nucleotides (step 110). The presence of a separate wash step (110) may, in some embodiments, be preferable.

The identity of the labeled, blocked nucleotides incorporated into the copy strand during step 100 is then detected in the presence of the mixture of blocked, unlabeled nucleotides (130) in a "detection step." The labeled, unblocked nucleotides may be incorporated into copy strands that are lagging and out of phase. That is, if a blocked, labeled nucleotide was not incorporated into the copy strand during step 100, a blocked, unlabeled nucleotide may be incorporated during the detection step 130 to bring lagging copy strands back into phase.

The components of the composition comprising the blocked, unlabeled nucleotides should not substantially interfere with the detection of the identity of the incorporated labeled nucleotide. For example, if labeled nucleotides comprise fluorescent labels, the components of the composition preferably do not produce a fluorescent signal under conditions that result in a fluorescent signal from the labeled nucleotides, and the components of the composition preferably do not interfere with the fluorescent signal produced by the labeled nucleotide.

The time that the composition comprising the blocked, labeled nucleotides is incubated with the template strands during the detection step is preferably sufficient to reduce phasing. Preferably, the length of the detection step is not increased to allow additional time for incorporation of the blocked, labeled nucleotides. That is, the duration of the detection steps is preferably a duration sufficient to detect the identity of the blocked, labeled nucleotide incorporated in the incorporation step.

While current sequencing methods may provide for lengthy detection steps, it is likely that much shorter detection steps may still allow for sufficient correction of phasing (i.e., incorporation of blocked, unlabeled nucleotide) even in less than optimum conditions. For example, 90 second detection steps are often used with Illumina MiniSeq™ sequencers. However, it is believed that much shorter detection times may be sufficient to allow incorporation of nucleotides into lagging strands during the detection step.

In some embodiments, the time that the composition comprising the blocked, labeled nucleotides is incubated with the template strands during a detection step is between 5 seconds and 120 seconds, such as between 10 seconds and 90 seconds. In some embodiments, the time that the composition comprising the blocked, labeled nucleotides is incubated with the template strands during a detection step is 120 seconds or less, such as 60 seconds or less, 30 seconds or less, 10 seconds or less, or 5 seconds or less. In some embodiments, the time that the composition comprising the blocked, labeled nucleotides is incubated with the template strands during a detection step is 1 second or more, such as 5 seconds or more, or 10 seconds or more.

Still referring to FIGS. 1-2, in step 140, the method may further include unblocking and un-labeling any labeled, blocked nucleotides incorporated into the copy strand in step 100 and unblocking any unlabeled, blocked nucleotides incorporated into the copy strand in step 130. The unblocking step involves removing a blocking moiety from the last incorporated nucleotide in the copy strand and the detectable moiety is cleaved from or masked on the last nucleotide incorporated into the copy strand.

A wash step (not shown) may be performed between steps 130 and 140 or after step 140, or both.

Following the unblocking and un-labeling (140), the process may be repeated until a predetermined number of cycles have been run or sequencing is completed.

Alternatively, a mixture of blocked, labeled nucleotides, without a chain extending enzyme, may be introduced to the site comprising the multiple template polynucleotide strands (150) and the process may be repeated, beginning at step 110. The chain extending enzyme may remain at the site. For example, the chain extending enzyme be bound to the template strand, the copy strand or both, and may remain active for multiple sequencing cycles. However, it is preferred, in some embodiments, to introduce additional chain extending enzyme along with the mixture of blocked, labeled nucleotides (100) as the amount of functional chain extending enzyme tends to be decreased following the unblocking and un-labelling step (140).

As shown in FIG. 2 at step 125, a second chain extending enzyme, which may be the same enzyme or a different enzyme from the first chain extending enzyme introduced at step 100, may be included with the composition comprising the mixture of blocked, unlabeled nucleotides and introduced to the site comprising the multiple template strands. Step 125 in FIG. 2 may replace step 120 in one or more cycles of the process of FIG. 1. Surprisingly, it has been found that less phasing may occur if a second chain extending enzyme is not added (e.g., as indicated in step 120 in FIG. 1) than if a second chain extending enzyme is added at step 125.

In the provided methods, the steps of nucleotide incorporation and detection can be repeated one or more times. For example, the steps can be repeated at least 25 times in some embodiments, at least 75 times in other embodiments, and at least 100 times in yet other embodiments. Thus, the provided methods include, but are not limited to, repeating the incorporating and detection steps for a number of cycles in a range from between about 100 cycles to about 1,000 cycles, in some embodiments, from between about 100 cycles to about 500 cycles, in other embodiments, and from between about 100 cycles to about 300 cycles, in yet other embodiments.

The sequencing methods described herein may be performed in any suitable manner, using any suitable equipment. In some embodiments, the sequencing methods employ a solid support on which the multiple template polynucleotide strands are immobilized. The term immobilized as used herein is intended to encompass direct or indirect attachment to a solid support via covalent or non-covalent bond(s). In particular embodiments, all that is required is that the polynucleotides remain immobilized or attached to a support under conditions in which it is intended to use the support, for example in applications requiring nucleic acid amplification and/or sequencing. For example, oligonucleotides or primers may be immobilized such that a 3' end is available for enzymatic extension and/or at least a portion of the sequence is capable of hybridizing to a complementary sequence. Immobilization can occur via hybridization to a surface attached primer, in which case the immobilized primer or oligonucleotide may be in the 3'-5' orientation. Alternatively, immobilization may occur by non-base-pairing hybridization, such as the covalent attachment.

By way of example, the polynucleotides may be attached to the surface by hybridization or annealing to one or more primers in a patch of primers. Hybridization may be accomplished, for example, by ligating an adapter to the ends of the template polynucleotides. The nucleic acid sequence of the adapter can be complementary to the nucleic acid sequence of the primer, thus, allowing the adapter to bind or hybridize to the primer on the surface. Optionally, the polynucleotides may be single- or double-stranded and adapters may be added to the 5' and/or 3' ends of the polynucleotides. Optionally, the polynucleotides may be double-stranded, and adapters may be ligated onto the 3' ends of double-stranded polynucleotide. Optionally, polynucleotides may be used without any adapter. In some embodiments, template polynucleotides may be attached to a surface by interactions other than hybridization to a complementary primer. For example, a polynucleotide may be covalently attached to a surface using a chemical linkage such as those resulting from click chemistry or a receptor-ligand interaction such as streptavidin-biotin binding.

Primer oligonucleotides, oligonucleotide primers and primers are used throughout interchangeably and are polynucleotide sequences that are capable of annealing specifically to one or more polynucleotide templates to be amplified or sequenced. Generally, primer oligonucleotides are single-stranded or partially single-stranded. Primers may also contain a mixture of non-natural bases, non-nucleotide chemical modifications or non-natural backbone linkages so long as the non-natural entities do not interfere with the function of the primer. Optionally, a patch of primers on a surface of a solid support may comprise one or more different pluralities of primer molecules. By way of example, a patch may comprise a first, second, third, fourth, or more pluralities of primer molecules each plurality having a different sequence. It will be understood that for embodiments having different pluralities of primers in a single patch, the different pluralities of primers may share a common sequence so long as there is a sequence difference between at least a portion of the different pluralities. For example, a first plurality of primers may share a sequence with a second plurality of primers as long the primers in one plurality have a different sequence not found in the primers of the other plurality.

The template polynucleotides may be amplified on the surface of the solid support. Polynucleotide amplification includes the process of amplifying or increasing the numbers of a polynucleotide template and/or of a complement thereof that are present, by producing one or more copies of the template and/or or its complement. Amplification may be carried out by a variety of known methods under conditions including, but not limited to, thermocycling amplification or isothermal amplification. For example, methods for carrying out amplification are described in U.S. Publication No. 2009/0226975; WO 98/44151; WO 00/18957; WO 02/46456; WO 06/064199; and WO 07/010251; which are incorporated by reference herein in their entireties. Briefly, in the provided methods, amplification can occur on the surface to which the polynucleotide molecules are attached. This type of amplification can be referred to as solid phase amplification, which when used in reference to polynucleotides, refers to any polynucleotide amplification reaction carried out on or in association with a surface (e.g., a solid support). Typically, all or a portion of the amplified products are synthesized by extension of an immobilized primer. Solid phase amplification reactions are analogous to standard solution phase amplifications except that at least one of the amplification primers is immobilized on a surface (e.g., a solid support).

Suitable conditions include providing appropriate buffers/solutions for amplifying polynucleotides. Such solutions include, for example, an enzyme with polymerase activity, nucleotide triphosphates, and, optionally, additives such as DMSO or betaine. Optionally, amplification is carried out in the presence of a recombinase agent as described in U.S. Pat. No. 7,485,428, which is incorporated by reference herein in its entirety, which allows for amplification without thermal melting. Briefly, recombinase agents such as the RecA protein from *E. coli* (or a RecA relative from other phyla), in the presence of, for example, ATP, dATP, ddATP, UTP, or ATPγS, will form a nucleoprotein filament around single-stranded DNA (e.g., a primer). When this complex comes in contact with homologous sequences the recombinase agent will catalyze a strand invasion reaction and pairing of the primer with the homologous strand of the target DNA. The original pairing strand is displaced by strand invasion leaving a bubble of single stranded DNA in the region, which serves as a template for amplification.

Solid-phase amplification may comprise a polynucleotide amplification reaction comprising only one species of oligonucleotide primer immobilized to a surface. Alternatively, the surface may comprise a plurality of first and second different immobilized oligonucleotide primer species. Solid phase nucleic acid amplification reactions generally comprise at least one of two different types of nucleic acid amplification, interfacial and surface (or bridge) amplification. For instance, in interfacial amplification the solid support comprises a template polynucleotide that is indirectly immobilized to the solid support by hybridization to an immobilized oligonucleotide primer, the immobilized primer may be extended in the course of a polymerase-catalyzed, template-directed elongation reaction (e.g., primer extension) to generate an immobilized polynucleotide that remains attached to the solid support. After the extension phase, the polynucleotides (e.g., template and its complementary product) are denatured such that the template polynucleotide is released into solution and made available for hybridization to another immobilized oligonucleotide primer. The template polynucleotide may be made available in 1, 2, 3, 4, 5 or more rounds of primer extension or may be washed out of the reaction after 1, 2, 3, 4, 5 or more rounds of primer extension.

In surface (or bridge) amplification, an immobilized polynucleotide hybridizes to an immobilized oligonucleotide primer. The 3' end of the immobilized polynucleotide provides the template for a polymerase-catalyzed, template-directed elongation reaction (e.g., primer extension) extending from the immobilized oligonucleotide primer. The resulting double-stranded product "bridges" the two primers and both strands are covalently attached to the support. In the next cycle, following denaturation that yields a pair of single strands (the immobilized template and the extended-primer product) immobilized to the solid support, both immobilized strands can serve as templates for new primer extension.

Amplification may be used to produce colonies of immobilized polynucleotides. For example, the methods can produce clustered arrays of polynucleotide colonies, analogous to those described in U.S. Pat. No. 7,115,400; U.S. Publication No. 2005/0100900; WO 00/18957; and WO 98/44151, which are incorporated by reference herein in their entireties. "Clusters" and "colonies" are used interchangeably and refer to a plurality of copies of a polynucleotide having the same sequence and/or complements thereof attached to a surface. Typically, the cluster comprises a plurality of copies of a polynucleotide having the same sequence and/or complements thereof, attached via their 5' termini to the surface. The copies polynucleotides making up the clusters may be in a single or double stranded form.

Thus, the plurality of template polynucleotides may be in a cluster, each cluster containing template polynucleotides of the same sequence. A plurality of clusters can be sequenced, each cluster comprising polynucleotides of the same sequence. Optionally, the sequence of the polynucleotides in a first cluster is different from the sequence of the nucleic acid molecules of a second cluster. Optionally, the cluster is formed by annealing to a primer on a solid surface a template polynucleotide and amplifying the template polynucleotide under conditions to form the cluster comprising the plurality of template polynucleotides of the same sequence. Amplification can be thermal or isothermal.

Each colony may comprise polynucleotides of the same sequences. In particular embodiments, the sequence of the polynucleotides of one colony is different from the sequence of the polynucleotides of another colony. Thus, each colony comprises polynucleotides having different nucleic acid sequences. All the immobilized polynucleotides in a colony are typically produced by amplification of the same polynucleotide. In some embodiments, it is possible that a colony of immobilized polynucleotides contains one or more primers without an immobilized polynucleotide to which another polynucleotide of different sequence may bind upon additional application of solutions containing free or unbound polynucleotides. However, due to the lack of sufficient numbers of free primers in a colony, this second or invading polynucleotide may not amplify to significant numbers. The second or invading polynucleotide typically is less than 1, 0.5, 0.25, 0.1, 0.001 or 0.0001% of the total population of polynucleotides in a single colony. Thus, the second or invading polynucleotide may not be optically detected or detection of the second or invading polynucleotide is considered background noise or does not interfere with detection of the original, immobilized polynucleotides in the colony. In such embodiments, the colony will be apparently homogeneous or uniform in accordance with the resolution of the methods or apparatus used to detect the colony.

The clusters may have different shapes, sizes and densities depending on the conditions used. For example, clusters may have a shape that is substantially round, multi-sided, donut-shaped or ring-shaped. The diameter or maximum cross section of a cluster may be from about 0.2 µm to about 6 µm, about 0.3 µm to about 4 µm, about 0.4 µm to about 3 µm, about 0.5 µm to about 2 µm, about 0.75 µm to about 1.5 µm, or any intervening diameter. Optionally, the diameter or maximum cross section of a cluster may be at least about 0.5 µm, at least about 1 µm, at least about 1.5 µm, at least about 2 µm, at least about 2.5 µm, at least about 3 µm, at least about 4 µm, at least about 5 µm, or at least about 6 µm. The diameter of a cluster may be influenced by a number of parameters including, but not limited to, the number of amplification cycles performed in producing the cluster, the length of the polynucleotide template, the GC content of the polynucleotide template, the shape of a patch to which the primers are attached, or the density of primers attached to the surface upon which clusters are formed. However, as discussed above, in all cases, the diameter of a cluster may be no larger than the patch upon which the cluster is formed. For example, if a patch is a bead, the cluster size will be no larger than the surface area of the bead. The density of clusters can be in the range of at least about $0.1/mm^2$, at least about $1/mm^2$, at least about $10/mm^2$, at least about $100/mm^2$, at least about $1,000/mm^2$, at least about $10,000/mm^2$ to at least about $100,000/mm^2$. Optionally, the clusters have a density of, for example, $100,000/mm^2$ to $1,000,000/mm^2$ or $1,000,000/mm^2$ to $10,000,000/mm^2$. The methods provided herein can produce colonies that are of approximately equal size. This occurs regardless of the differences in efficiencies of amplification of the polynucleotides of different sequence.

Clusters may be detected, for example, using a suitable imaging means, such as, a confocal imaging device or a charge coupled device (CCD) or CMOS camera. Exemplary imaging devices include, but are not limited to, those described in U.S. Pat. Nos. 7,329,860; 5,754,291; and 5,981, 956; and WO 2007/123744, each of which is herein incorporated by reference in its entirety. The imaging apparatus may be used to determine a reference position in a cluster or in a plurality of clusters on the surface, such as the location, boundary, diameter, area, shape, overlap and/or center of one or a plurality of clusters (and/or of a detectable signal originating therefrom). Such a reference position may be recorded, documented, annotated, converted into an interpretable signal, or the like, to yield meaningful information.

As used herein, the term "support" refers to a substrate for attaching polynucleotides. A support is a material having a rigid or semi-rigid surface to which a polynucleotide can be attached or upon which nucleic acids can be synthesized and/or modified. Supports can include any resin, gel, bead, well, column, chip, flowcell, membrane, matrix, plate, filter, glass, controlled pore glass (CPG), polymer support, membrane, paper, plastic, plastic tube or tablet, plastic bead, glass bead, slide, ceramic, silicon chip, multi-well plate, nylon membrane, fiber optic, and PVDF membrane.

A support may include any flat wafer-like substrates and flat substrates having wells, such as a microtiter plate, including 96-well plates. Exemplary flat substrates include chips, slides, etched substrates, microtiter plates, and flow cell reactors, including multi-lane flow cell reactors having multiple microfluidic channels, such as the eight-channel flow cell used in the cBot sequencing workstation (Illumina, Inc., San Diego, Calif.). Exemplary flow cells are described in WO 2007/123744, which is incorporated herein by reference in its entirety. Optionally, the flowcell is a patterned flowcell. Suitable patterned flowcells include, but are not limited to, flowcells described in WO 2008/157640, which is incorporated by reference herein in its entirety.

A support may also include beads, including magnetic beads, hollow beads, and solid beads. Beads may be used in conjunction with flat supports, such flat supports optionally also containing wells. Beads, or alternatively microspheres, refer generally to a small body made of a rigid or semi-rigid material. The body may have a shape characterized, for example, as a sphere, oval, microsphere, or other recognized particle shape whether having regular or irregular dimensions. The sizes of beads, in particular, include, without limitation, about 1 µm, about 2 µm, about 3 µm, about 5 µm, about 10 µm, about 20 µm, about 30 µm, about 40 µm, about 60 µm, about 100 µm, about 150 µm or about 200 µm in diameter. Other particles may be used in ways similar to those described herein for beads and microspheres.

The composition of a support may vary depending, for example, on the format, chemistry and/or method of attachment and/or on the method of nucleic acid synthesis. Support materials that can be used in accordance with the present disclosure include, but are not limited to, polypropylene, polyethylene, polybutylene, polyurethanes, nylon, metals, and other suitable materials. Exemplary compositions include supports, and chemical functionalities imparted thereto, used in polypeptide, polynucleotide and/or organic moiety synthesis. Such compositions include, for example, plastics, ceramics, glass, polystyrene, melamine, methylstyrene, acrylic polymers, paramagnetic materials, thoria sol, carbon graphite, titanium dioxide, latex or cross-linked dextrans such as Sepharose™, cellulose, nylon, cross-linked micelles and Teflon™, as well as any other materials which can be found described in, for example, "*Microsphere Detection Guide*" from Bangs Laboratories, Fishers Ind., which is incorporated herein by reference. A support particle may be made of cross-linked starch, dextrans, cellulose, proteins, organic polymers including styrene polymers including polystyrene and methylstyrene as well as other styrene co-polymers, plastics, glass, ceramics, acrylic polymers, magnetically responsive materials, colloids, thoriasol, carbon graphite, titanium dioxide, nylon, latex, or TEFLON®. "Microsphere Detection Guide" from Bangs Laboratories, Fishers, Inc., hereby incorporated by reference in its entirety, is a helpful guide. Further exemplary supports within the scope of the present disclosure include, for example, those described in US Application Publication Ser. No. 02/0102,578 and U.S. Pat. No. 6,429,027, both of which are incorporated herein by reference in their entirety.

Figure 3:
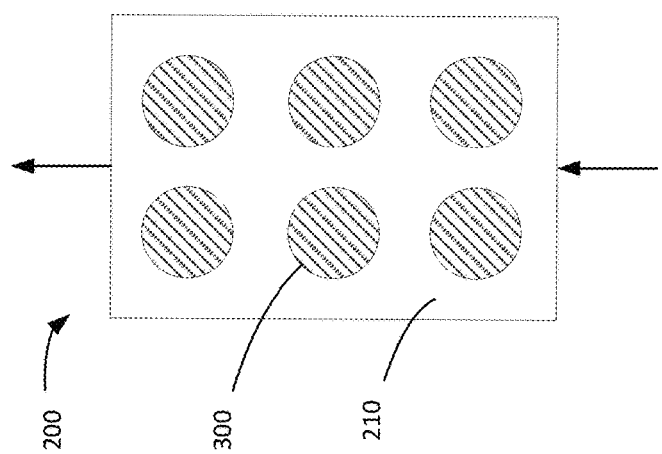
FIG. 3 is a schematic plan view of an embodiment of a flow cell that may be employed in accordance with the teachings presented herein.

For example, and with reference to FIG. 3, an embodiment of a solid support 200, such as a flow cell, is shown. The solid support 200 has a surface 210 to which clusters 300 containing multiple template polynucleotide strands having the same nucleotide sequence are bound. The surface 210 of the solid support 200 may be planar.

Fluid compositions containing reagents, wash buffers, and the like may flow over the surface 210 of the solid support 200 to interact with the template polynucleotides in the clusters 300. The flow of the compositions may occur in any direction, such as the direction indicated by the arrows in FIG. 3.

Sequencing apparatus with which the flow cell 300 may be used may be configured to flow reagents and compositions across the surface 210 to interact with the template strands in the clusters 300. For example, the apparatus may cause chain extending enzymes, sequencing primers, nucleotides, wash compositions, unblocking reagents, unlabeling reagents, and the like to flow across the surface 210 of the solid support 200, such as a flow cell, to interact with the template polynucleotides in the clusters 300 at the appropriate times to carry out sequencing of the template strands.

Each cluster 300 may contain the same template polynucleotides or different polynucleotides than another cluster 300.

The template polynucleotides to be sequenced may be obtained from any biological sample using known, routine methods. Suitable biological samples include, but are not limited to, a blood sample, biopsy specimen, tissue explant, organ culture, biological fluid or any other tissue or cell preparation, or fraction or derivative thereof or isolated therefrom. The biological sample can be a primary cell culture or culture adapted cell line including but not limited to genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, stem cells, germ cells (e.g. sperm, oocytes), transformed cell lines and the like. For example, polynucleotide molecules may be obtained from primary cells, cell lines, freshly isolated cells or tissues, frozen cells or tissues, paraffin embedded cells or tissues, fixed cells or tissues, and/or laser dissected cells or tissues. Biological samples can be obtained from any subject or biological source including, for example, human or non-human animals, including mammals and non-mammals, vertebrates and invertebrates, and may also be any multicellular organism or single-celled organism such as a eukaryotic (including plants and algae) or prokaryotic organism, archaeon, microorganisms (e.g. bacteria, archaea, fungi, protists, viruses), and aquatic plankton.

Once the polynucleotides are obtained, a plurality of polynucleotides molecules of different sequence for use in the provided methods may be prepared using a variety of standard techniques available and known. Exemplary methods of polynucleotide molecule preparation include, but are not limited to, those described in Bentley et al., Nature 456:49-51 (2008); U.S. Pat. No. 7,115,400; and U.S. Patent Application Publication Nos. 2007/0128624; 2009/0226975; 2005/0100900; 2005/0059048; 2007/0110638; and 2007/0128624, each of which is herein incorporated by reference in its entirety. The template polynucleotides may contain a variety of sequences including, but not limited to, universal sequences and known or unknown sequences. For example, polynucleotide may comprise one or more regions of known sequence (e.g., an adaptor) located on the 5' and/or 3' ends. Such template polynucleotides may be formed by attaching adapters to the ends of a polynucleotides of unknown sequence. When the polynucleotides comprise known sequences on the 5' and 3' ends, the known sequences may be the same or different sequences. Optionally, a known sequence located on the 5' and/or 3' ends of the polynucleotides is capable of hybridizing to one or more primers immobilized on the surface. For example, a polynucleotide comprising a 5' known sequence may hybridize to a first plurality of primers while the 3' known sequence may hybridize to a second plurality of primers. Optionally, polynucleotides comprise one or more detectable labels. The one or more detectable labels may be attached to the polynucleotide template at the 5' end, at the 3' end, and/or at any nucleotide position within the polynucleotide molecule. The polynucleotides for use in the provided methods may comprise the polynucleotide to be amplified and/or sequenced and, optionally, short nucleic acid sequences at the 5' and/or 3' end(s).

A short nucleic acid sequence that is added to the 5' and/or 3' end of a polynucleotide may be a universal sequence. A universal sequence is a region of nucleotide sequence that is common to, i.e., shared by, two or more polynucleotides, where the two or more polynucleotides also have regions of sequence differences. A universal sequence that may be present in different members of a plurality of polynucleotides may allow the replication or amplification of multiple different sequences using a single universal primer that is complementary to the universal sequence. Similarly, at least one, two (e.g., a pair) or more universal sequences that may be present in different members of a collection of polynucleotides may allow the replication or amplification of multiple different sequences using at least one, two (e.g., a pair) or more single universal primers that are complementary to the universal sequences. Thus, a universal primer includes a sequence that may hybridize specifically to such a universal sequence. The polynucleotide may be modified to attach universal adapters (e.g., non-target nucleic acid sequences) to one or both ends of the different target sequences, the adapters providing sites for hybridization of universal primers. This approach has the advantage that it is not necessary to design a specific pair of primers for each polynucleotide to be generated, amplified, sequenced, and/or otherwise analyzed; a single pair of primers can be used for amplification of different polynucleotides provided that each polynucleotide is modified by addition of the same universal primer-binding sequences to its 5' and 3' ends.

The polynucleotides may also be modified to include any nucleic acid sequence desirable using standard, known methods. Such additional sequences may include, for example, restriction enzyme sites, or indexing tags in order to permit identification of amplification products of a given nucleic acid sequence.

As used herein, the term different when used in reference to two or more polynucleotides means that the two or more polynucleotides have nucleotide sequences that are not the same. For example, two polynucleotides can differ in the content and order of nucleotides in the sequence of one polynucleotide compared to the other polynucleotide. The term can be used to describe polynucleotides whether they are referred to as copies, amplicons, templates, targets, primers, oligonucleotides, or the like.

Referring now to FIGS. 4A-G, schematic drawings illustrating an embodiment of a sequencing method is shown. The depicted embodiment illustrates a problem with phasing, and how the method addresses the problem. In FIGS. 4A-G, a plurality of polynucleotides 400 having the same sequence are shown. The polynucleotides 400 may be bound to a surface of a solid support at their 3' or 5' ends. For example, the polynucleotides may be bound to the surface 210 in a cluster 300 on a flow cell 200 as depicted in FIG. 3.

Figure 4A:
FIGS. 4A-G are schematic drawings illustrating various cycles of sequencing and compensation for phasing during the scanning (detection) step.
Figure 4A:
Figure 4A:
Figure 4A:
Figure 4A:
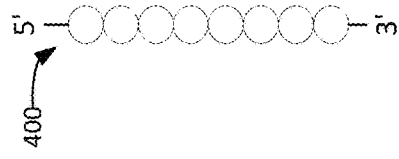

FIG. 4A shows the template polynucleotides 400 prior to the initiation of sequencing.

Figure 4B:
Figure 4B:
Figure 4B:
Figure 4B:
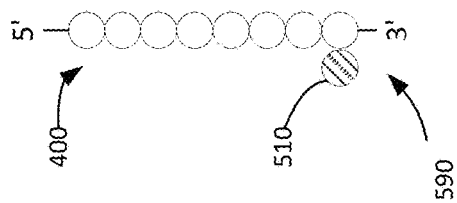

FIG. 4B shows a single blocked, labeled nucleotide 510 incorporated into a copy strand 590 during a first round of sequencing, such as after the wash step 110 of FIGS. 1-2. For convenience and clarity, the chain extending enzyme, which may remain on the template polynucleotides 400 after a wash step, is not shown. In some embodiments, a primer polynucleotide (not shown), complementary to a portion of the sequence of the template, may be used to facilitate incorporation of the nucleotides 510. In the embodiment depicted in FIG. 4B, a blocked, labeled nucleotide 510 is incorporated into copy strands 590 for four out of the five template polynucleotides 400. Without more, the strand in which no blocked, labeled nucleotide 510 was incorporated would be out of phase.

Figure 4C:
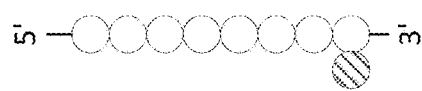
Figure 4C:
Figure 4C:
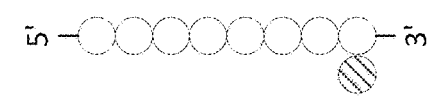
Figure 4C:
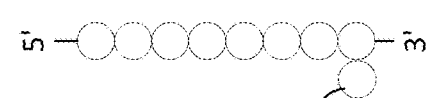
Figure 4C:
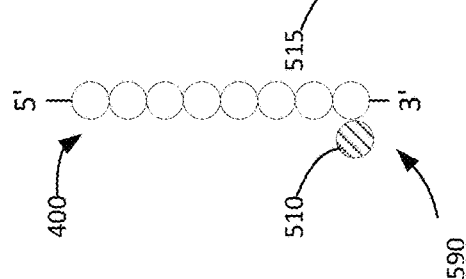

However, as shown in FIG. 4C, if blocked, unlabeled nucleotides (e.g., step 120 or 125 in FIG. 1 or FIG. 2) were incubated with the template polynucleotides 400 during detection of the identity of the blocked, labeled nucleotides 510 (e.g., step 130 of FIGS. 1-2), a blocked, unlabeled nucleotide 515 could be incorporated into the lagging strand to bring the lagging strand into phase prior to the next cycle of sequencing. As stated above, the blocked, unlabeled nucleotide 515 may be incorporated by a chain extending enzyme (not shown) that remains after a wash step (e.g., step 110 of FIGS. 1-2) or that is introduced with the mixture of unblocked, unlabeled nucleotides (e.g., step 125 of FIG. 2). The incorporated nucleotides 510, 515 may then be unblocked and unlabeled, in the case of nucleotides 510 (e.g., step 140 of FIGS. 1-2), and another cycle of sequencing may be performed.

Figure 4D:
Figure 4D:
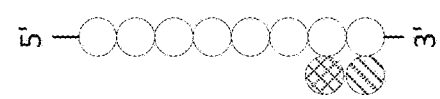
Figure 4D:
Figure 4D:
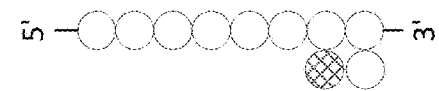
Figure 4D:
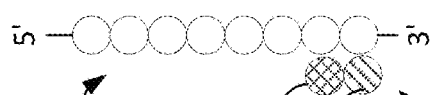

FIG. 4D shows incorporation of second blocked, labeled nucleotides 520 into the copy strand 590 following an incorporation step (such as step 100 of FIGS. 1-2) and a wash step (such as step 110 of FIGS. 1-2) in a second cycle of sequencing. In the embodiment depicted in FIG. 4D, a blocked, labeled nucleotide 520 is incorporated into copy strands 590 for four out of the five template polynucleotides 400. Without more, the copy strand 590 in which no blocked, labeled nucleotide 510 was incorporated would be out of phase.

Figure 4E:
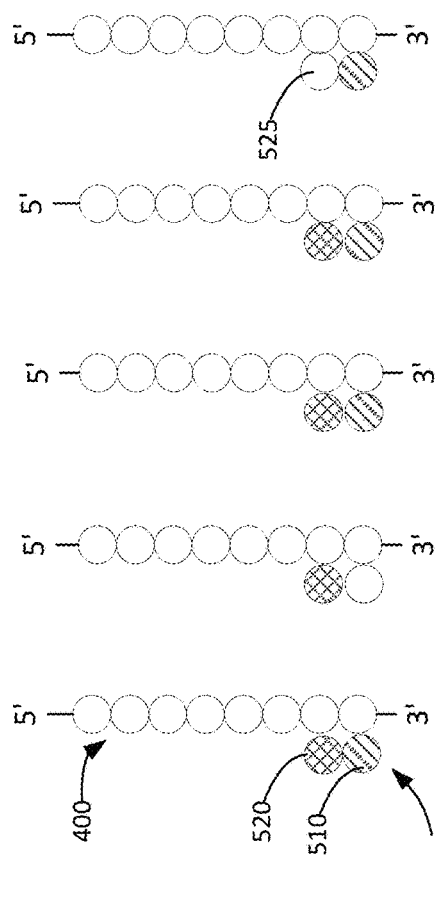

However, as shown in FIG. 4E, if blocked, unlabeled nucleotides (e.g., step 120 or 125 in FIG. 1 or FIG. 2) were incubated with the template polynucleotides 400 during detection of the identity of the blocked, labeled nucleotides 520 (e.g., step 130 of FIGS. 1-2), a blocked, unlabeled nucleotide 525 could be incorporated into the lagging strand to bring the lagging strand into phase prior to the next cycle of sequencing. The incorporated nucleotides 520, 525 may be unblocked and unlabeled, in the case of nucleotides 520 (e.g., step 140 of FIGS. 1-2) and another cycle of sequencing may be performed.

Figure 4F:
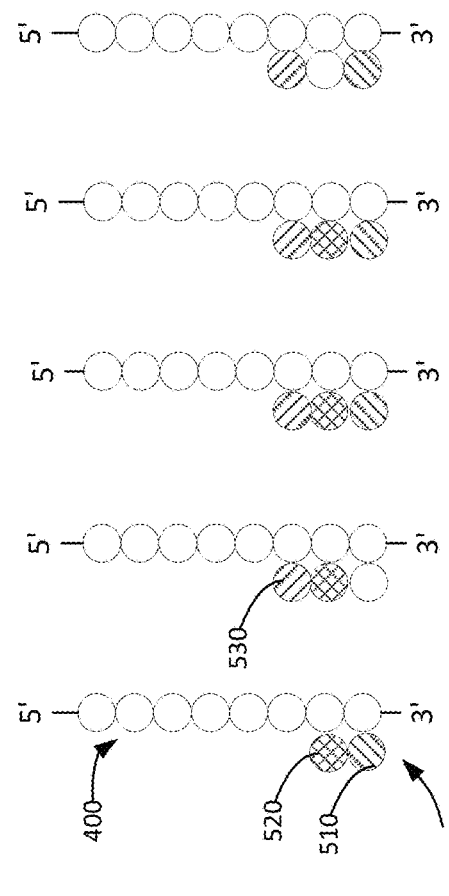
Figure 4G:
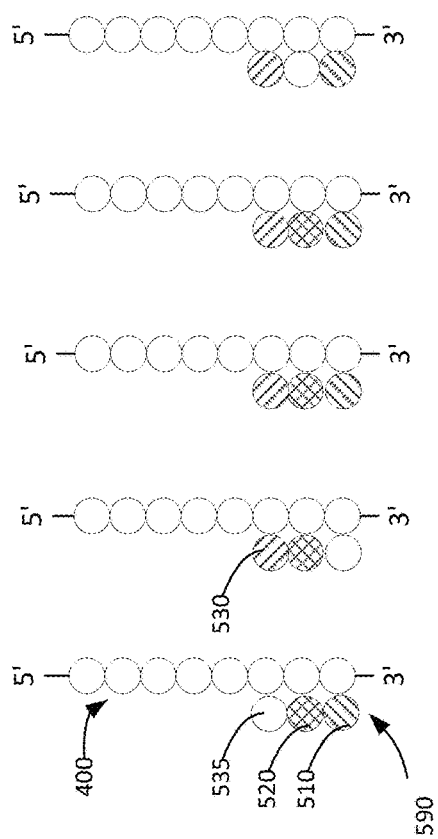

FIG. 4F illustrates another cycle of sequencing in which blocked, labeled nucleotides 530 are incorporated into four out of five copy strands 590 following an incorporation step. FIG. 4G illustrates incorporation of a blocked, unlabeled nucleotide 535 into the lagging strand to bring the lagging strand into phase prior to the next cycle of sequencing. After three cycles of sequencing as illustrated in FIG. 4G all the copy strands 590 are in phase. However, without incubating the blocked, unlabeled nucleotides during the detection step, three of the five strands would have been out of phase in the illustrated embodiment. With 60% of the copy strands being out of phase, the signal produced during the detection step would likely be too heterogeneous, due to incorporation of a different labeled nucleotide, to properly identify the appropriate nucleotide.

While the drawings presented in FIGS. 4A-G are schematic, they illustrate a few key points. For example, a small rate of phasing may be compounded over multiple cycles of sequencing. However, bringing lagging copy strands into phase during detection through the incorporation of unlabeled nucleotides does not require a great deal of chain extending activity due to the relatively low numbers of lagging strands after a round of incorporation. Thus, less than optimum conditions for incorporation of the unlabeled nucleotides may be tolerated for incorporation of the unlabeled nucleotides. Thus, conditions that are not intended to optimize the efficiency and accuracy of the chain extending enzyme may be tolerated.

Any suitable composition comprising the mixture of blocked, unlabeled nucleotides may be used. In some embodiments, the composition comprises a buffered solution having a pH from about 8 to about 10, such as from about 9 to about 9.5. Any suitable buffer, such as a Tris buffer, may be used. The blocked, unlabeled nucleotides may be present in any suitable concentration such as from about 0.001 to about 15 µM, such as from about 0.5 µM to about 5 µM, such as about 2 µM. The composition may comprise any suitable amount of a chelator, such as from about 0 mM to about 5 mM ethylenediaminetetraacetic acid (EDTA), or from about 0 mM to about 2 mM EDTA, or from about 0 mM to about 1 mM EDTA. The composition may comprise any suitable amount of magnesium sulfate, such as from about 1 mM to about 10 mM $MgSO_4$, from about 2 mM to about 6 mM $MgSO_4$, or about 4 mM $MgSO_4$. The composition may comprise any suitable amount of a detergent. For example, the composition may comprise from about 0.05% to about 1% detergent by weight, such as from about 0.1% to about 0.5% detergent by weight, or about 0.2% detergent by weight. Any suitable detergent may be used. For example, polyoxyethylenesorbitan monolaurate (also referred to as polyoxyethylenesorbitan monolaurate, or Tween) or 3-[(3-cholamidopropyl)dimethylammonio]-1-propanesulfonate hydrate (CHAPS) detergents may be used. The composition may comprise any suitable amount of an antioxidant. For example, the detergent may comprise one or more antioxidant in a combined total antioxidant concentration from about 1 mM to about 50 mM, such as from about 2 mM to about 40 mM, from about 3 mM to about 20 mM, or from about 15 mM to about 25 mM. Suitable antioxidants include ascorbate, acetovanillone, and Trolox. Preferably, the composition is free of labeled nucleotides.

In some embodiments, the composition comprising a mixture of blocked, unlabeled nucleotides comprises a Tris buffer, has a pH of about 9 to about 9.5, has a detergent, $MgSO_4$, EDTA, ascorbate, and acetovanillone. For example, the composition may include components as described in Table 1 below:

| REAGENT | CONCENTRATION |
| --- | --- |
| Tris buffer | 200 mM |
| pH | 9 to 9.5 |
| Blocked, unlabeled nucleotides | 2 µM each |
| CHAPS | 0.2% by weight |
| $MgSO_4$ | 4 mM |
| EDTA | 0 to 1 mM |
| Ascorbate | 3 to 20 mM |
| Acetovanillone | 10 to 15 mM |

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation may not be explicitly disclosed, each is specifically contemplated and described herein. For example, if a method is disclosed and discussed and a number of modifications that can be made to the method steps are discussed, each and every combination and permutation of the method steps, and the modifications that are possible are specifically contemplated unless specifically indicated to the contrary. Likewise, any subset or combination of these is also specifically contemplated and disclosed. This concept applies to all aspects of this disclosure. Thus, if there are a variety of additional steps that can be performed it is understood that each of these additional steps can be performed with any specific method steps or combination of method steps of the disclosed methods, and that each such combination or subset of combinations is specifically contemplated and should be considered disclosed.

Throughout this application, various publications are referenced. The disclosures of these publications in their entireties are hereby incorporated by reference into this application.

EXAMPLES

Example 1. Increased Phasing Correlates with Decreased Incorporation Time

Figure 5:
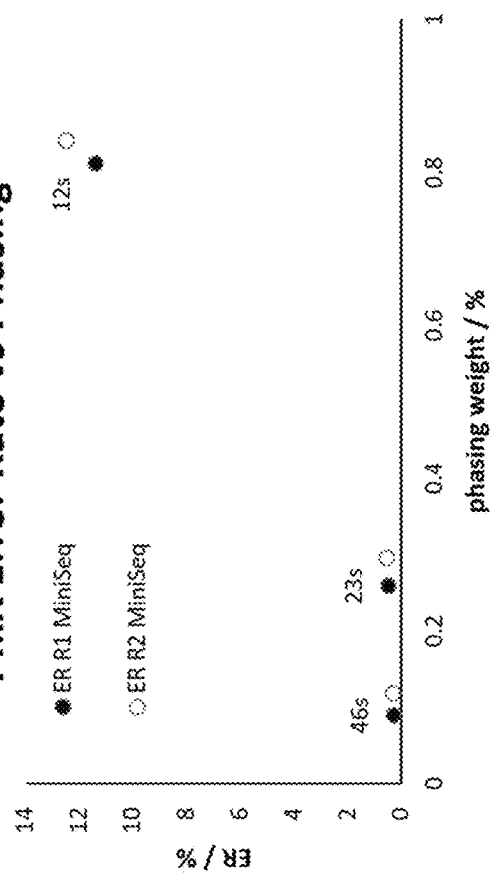
FIG. 5 is a plot illustrating the correlation between phasing (phasing weight %) and PhiX error rate (ER/%) using an Illumina MiniSeq™ sequencer with different incorporation times (46 seconds, 23 seconds, and 12 seconds).

To understand the effect of reduced incorporation time on phasing and error rate, sequencing of polypeptides of a known sequence were sequenced using an Illumina MiniSeq™ sequencer using different incorporation times. Specifically, the incorporation times were 46 seconds, 23 seconds, and 12 seconds. The correlation between phasing and error rate are shown in FIG. 5. As shown, error rate and phasing are kept low at long incorporation times (46 seconds). However, as the incorporate time decreases (e.g., 12 seconds), phasing and error rate increases. Accordingly, decreases in incorporation time tends to result in increased phasing and error rate.

Example 2. Decreased Phasing at Reduced Incorporation Times with Blocked, Unlabeled Nucleotides During Detection To evaluate whether phasing and error rate is affected by incubating with blocked, unlabeled nucleotides and polymerase during a detection step, a polynucleotide of a known sequence was sequenced using an Illumina MiniSeq™ sequencer using, during the detection step, (i) the manufacturer's scan mix (no blocked, unlabeled nucleotides and no polymerase—the "standard reagents"), and (ii) a modified scan mix that included blocked, unlabeled nucleotides and a polymerase ["ScanAndFill"]. The ScanAndFill mix included polymerase Po1812. 80 cycles of sequencing were run using incorporation times of 25 seconds and 7.5 seconds with the standard scan mix and an incorporation time 7.5 seconds with the ScanAndFill mix and the ScanAndFill mix. Error rate, phasing, and prephasing (where the copy strand incorporates an additional nucleotide beyond the in-phase copy strands) at each cycle was determined. The results are presented in FIG. 6 and Table 2 below.

TABLE 2

Error rate, phasing, and pre-phasing

| Scan Mix | Inc. Time | Density | % PF | % Align | Phasing | Prephasing | % Error |
|---|---|---|---|---|---|---|---|
| standard reagents | 2 × 25 s | 122 | 95.6 | 99.2 | 0.07 | 0.08 | 0.13 |
| standard reagents | 2 × 7.5 s | 122 | 95.6 | 99.2 | 0.65 | 0.04 | 0.86 |
| ScanAndFill | 2 × 7.5 s | 133 | 92.5 | 97.9 | 0.10 | 0.09 | 0.35 |

Figure 6:
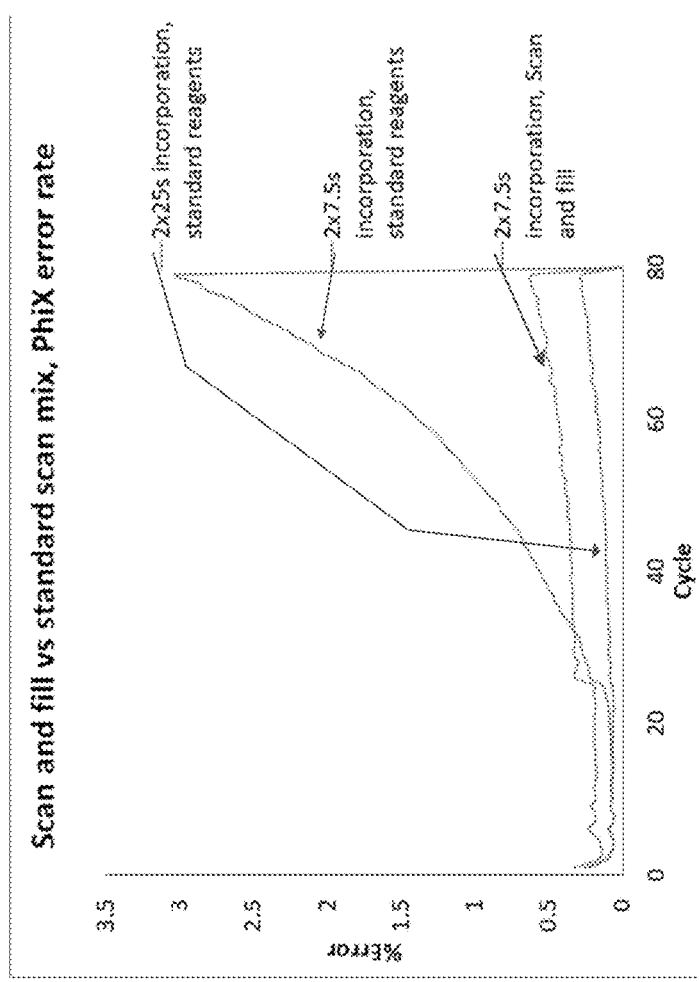
FIG. 6 is a plot of cumulative PhiX error rates over 80 cycles of sequencing in which no blocked, unlabeled nucleotides were used (standard scan mix) during a detection step or used blocked, unlabeled nucleotides were used (ScanAndFill mix) during the detection step.

As shown in FIG. 6 and Table 2, the use of the ScanAndFill mix yielded metrics somewhat comparable with baseline (standard reagents at 2×25 seconds) while reducing the total chemistry time per cycle by about 32% (112 seconds to 77 seconds). As indicated in Table 2, the reduction in error rate seems to be due to a reduction in phasing.

Figure 7:
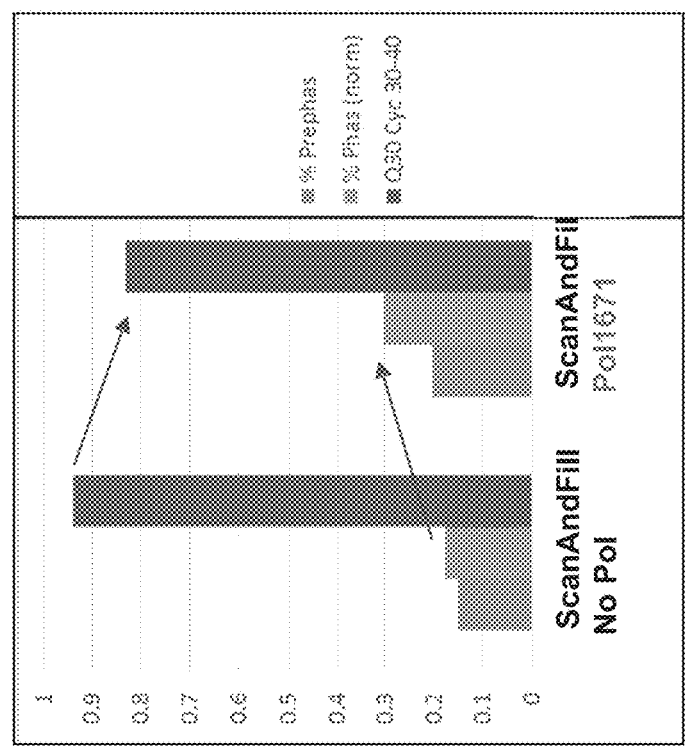
FIG. 7 is a bar graph of phasing, prephasing, and % Q30 rates over 40 cycles of sequencing in which blocked, unlabeled nucleotides were used (ScanAndFill), with additional polymerase (Pol1671) or no additional polymerase (No Pol), during the detection step.

Example 3. Decreased Phasing at Reduced Incorporation Times with Blocked, Unlabeled Nucleotides During Detection without Additional Polymerase To evaluate the effect of added polymerase in the ScanAndFill mix on phasing, prephasing and error rate, a polynucleotide of a known sequence was sequenced using an Illumina MiniSeg™ sequencer using, during the detection step, a ScanAndFill mix with and without polymerase. The ScanAndFill mixes were the same, except that the mix with the polymerase included 60 μg/ml Pol1671, which is described in provisional U.S. Patent Application No. 62/753,558, entitled "Polymerases, compositions, and methods of use," filed Oct. 31, 2018, the entire content of which is incorporated herein by reference. U.S. Pat. No. 11,104,888 and International Published Patent Application WO 2020/092830 claim priority to U.S. Patent Application No. 62/753,558. SEQ ID NO: 1 of U.S. Patent Application No. 62/753,558 has the following sequence: Met Ile Leu Asp Thr Asp Tyr Ile Thr Glu Asn Gly Lys Pro Val Ile Arg Val Phe Lys Lys Glu Asn Gly Glu Phe Lys Ile Glu Tyr Asp Arg Thr Phe Glu Pro Tyr Phe Tyr Ala Leu Leu Lys Asp Asp Ser Ala Ile Glu Asp Val Lys Lys Val Thr Ala Lys Arg His Gly Thr Val Val Lys Val Lys Arg Ala Glu Lys Val Gln Lys Lys Phe Leu Gly Arg Pro Ile Glu Val Trp Lys Leu Tyr Phe Asn His Pro Gln Asp Val Pro Ala Ile Arg Asp Arg Ile Arg Ala His Pro Ala Val Val Asp Ile Tyr Glu Tyr Asp Ile Pro Phe Ala Lys Arg Tyr Leu Ile Asp Lys Gly Leu Ile Pro Met Glu Gly Asp Glu Glu Leu Thr Met Leu Ala Phe Asp Ile Glu Thr Leu Tyr His Glu Gly Glu Glu Phe Gly Thr Gly Pro Ile Leu Met Ile Ser Tyr Ala Asp Gly Ser Glu Ala Arg Val Ile Thr Trp Lys Lys Ile Asp Leu Pro Tyr Val Asp Val Val Ser Thr Glu Lys Glu Met Ile Lys Arg Phe Leu Arg Val Val Arg Glu Lys Asp Pro Asp Val Leu Ile Thr Tyr Asn Gly Asp Asn Phe Asp Phe Ala Tyr Leu Lys Lys Arg Cys Glu Glu Leu Gly Ile Lys Phe Thr Leu Gly Arg Asp Gly Ser Glu Pro Lys Ile Gln Arg Met Gly Asp Arg Phe Ala Val Glu Val Lys Gly Arg Ile His Phe Asp Leu Tyr Pro Val Ile Arg Arg Thr Ile Asn Leu Pro Thr Tyr Thr Leu Glu Ala Val Tyr Glu Ala Val Phe Gly Lys Pro Lys Glu Lys Val Tyr Ala Glu Glu Ile Ala Gln Ala Trp Glu Ser Gly Glu Gly Leu Glu Arg Val Ala Arg Tyr Ser Met Glu Asp Ala Lys Val Thr Tyr Glu Leu Gly Arg Glu Phe Phe Pro Met Glu Ala Gln Leu Ser Arg Leu Ile Gly Gln Ser Leu Trp Asp Val Ser Arg Ser Ser Thr Gly Asn Leu Val Glu Trp Phe Leu Leu Arg Lys Ala Tyr Lys Arg Asn Glu Leu Ala Pro Asn Lys Pro Asp Glu Arg Glu Leu Ala Arg Arg Arg Gly Gly Tyr Ala Gly Gly Tyr Val Lys Glu Pro Glu Arg Gly Leu Trp Asp Asn Ile Val Tyr Leu Asp Phe Arg Ser Leu Tyr Pro Ser Ile Ile Ile Thr His Asn Val Ser Pro Asp Thr Leu Asn Arg Glu Gly Cys Lys Glu Tyr Asp Val Ala Pro Glu Val Gly His Lys Phe Cys Lys Asp Phe Pro Gly Phe Ile Pro Ser Leu Leu Gly Asp Leu Leu Glu Glu Arg Gln Lys Ile Lys Arg Lys Met Lys Ala Thr Val Asp Pro Leu Glu Lys Lys Leu Leu Asp Tyr Arg Gln Arg Ala Ile Lys Ile Leu Ala Asn Ser Phe Tyr Gly Tyr Tyr Gly Tyr Ala Lys Ala Arg Trp Tyr Cys Lys Glu Cys Ala Glu Ser Val Thr Ala Trp Gly Arg Glu Tyr Ile Glu Met Val Ile Arg Glu Leu Glu Glu Lys Phe Gly Phe Lys Val Leu Tyr Ala Asp Thr Asp Gly Leu His Ala Thr Ile Pro Gly Ala Asp Ala Glu Thr Val Lys Lys Lys Ala Lys Glu Phe Leu Lys Tyr Ile Asn Pro Lys Leu Pro Gly Leu Leu Glu Leu Glu Tyr Glu Gly Phe Tyr Val Arg Gly Phe Phe Val Thr Lys Lys Lys Tyr Ala Val Ile Asp Glu Glu Gly Lys Ile Thr Thr Arg Gly Leu Glu Ile Val Arg Arg Asp Trp Ser Glu Ile Ala Lys Glu Thr Gln Ala Arg Val Leu Glu Ala Ile Leu Lys His Gly Asp Val Glu Glu Ala Val Arg Ile Val Lys Glu Val Thr Glu Lys Leu Ser Lys Tyr Glu Val Pro Pro Glu Lys Leu Val Ile His Glu Gln Ile Thr Arg Asp Leu Arg Asp Tyr Lys Ala Thr Gly Pro His Val Ala Val Ala Lys Arg Leu Ala Ala Arg Gly Val Lys Ile Arg Pro Gly Thr Val Ile Ser Tyr Ile Val Leu Lys Gly Ser Gly Arg Ile Gly Asp Arg Ala Ile Pro Ala Asp Glu Phe Asp Pro Thr Lys His Arg Tyr Asp Ala Glu Tyr Tyr Ile Glu Asn Gln Val Leu Pro Ala Val Glu Arg Ile Leu Lys Ala Phe Gly Tyr Arg Lys Glu Asp Leu Arg Tyr Gln Lys Thr Lys Gln Val Gly Leu Gly Ala Trp Leu Lys Val Lys Gly Lys Lys (SEQ ID NO: 1). The other components of the ScanAndFill mixes were EA buffer; pH 9.85; MgSO4; EDTA; A, C, and T nucleotide triphosphates modified to include a fluorescent dye with a cleavable LN3 linker as described, for example, in U.S. Published Patent Application Nos. 2013/0079232 and 2016/0040225 (A-LN3, C-LN3, and T-LN3); Dark (unlabeled) G, and CHAPS. An incorporation time of 7.5 seconds was used. Q30, phasing, and prephasing values at each cycle were calculated. "Q30" refers to the percentage of reads that pass the Q30 quality filter, i.e. an error rate of less of equal to 1 in 1000, or 0.1%. The results are presented in FIG. 7.

As shown, phasing remained low in the presence and absence of added polymerase, suggesting that the polymerase from the incorporation step remained active and present during the detection step. Surprisingly, a lower rate of phasing was observed in the absence of additional polymerase. The overall error rate was reduced, as reflected in the higher Q30 value, as was the rate of phasing and pre-phasing.

Example 4. Addition of Antioxidant Further Reduces Error Rate and Signal Decay

Figure 9:
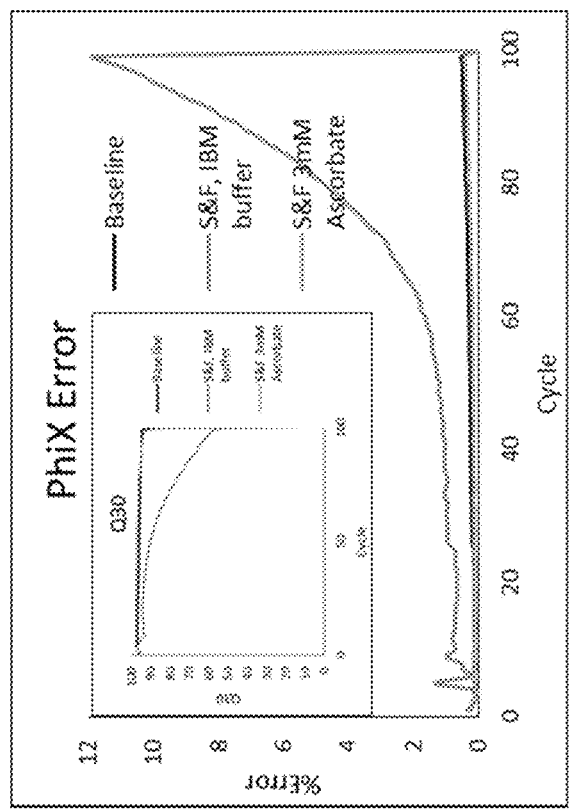
FIG. 9 is a plot of cumulative PhiX error rate (% Error, % Q30—inset) observed over 100 cycles of sequencing in which blocked, unlabeled nucleotides (S&F) were used during the detection step in the presence and absence of 3 mM ascorbate.
Figure 8:
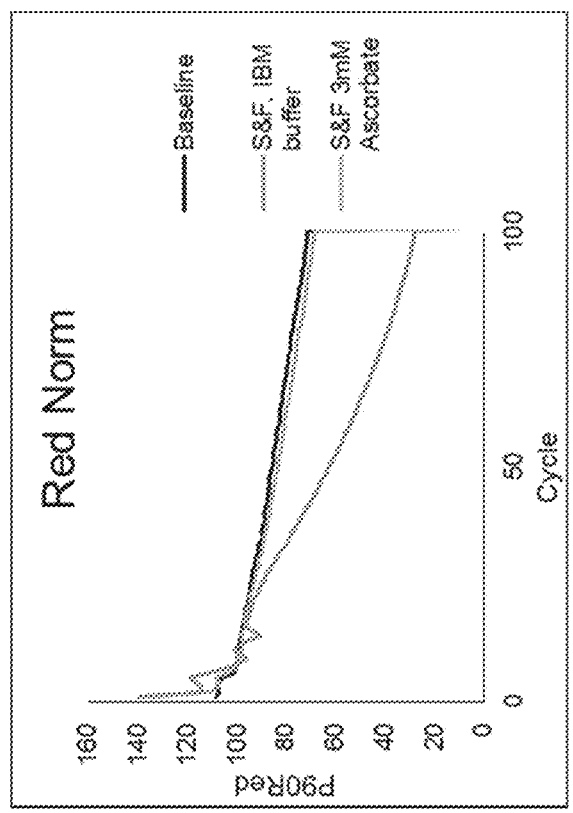
FIG. 8 is a plot of signal decay (P90Red) observed over 100 cycles of sequencing in which blocked, unlabeled nucleotides (S&F) were used during the detection step in the presence and absence of 3 mM ascorbate, which protects DNA from oxidative damage caused by the optical scanning.

To evaluate the effect of an added antioxidant in the ScanAndFill mix (no polymerase) on detection step signal decay and sequencing error rate, a polynucleotide of a known sequence was sequenced using an Illumina MiniSeq™ sequencer using, during the detection step, a ScanAndFill mix without a polymerase and with or without 3 mM ascorbate. The ScanAndFill mixes included EA buffer, pH 9.85, MgSO$_4$, EDTA, A-LN3, C-LN3, T-LN3, Dark G, and CHAPS. 100 cycles of sequencing were run using incorporation times of 7.5 seconds and were compared to a baseline using the standard scan mix with an incorporation time of 25 seconds per cycle. The results are shown in FIGS. 8-9.

The addition of ascorbate resulted in substantially improved signal decay reduction (FIG. 8) and reduction in error rate (FIG. 9) relative to the ScanAndFill without ascorbate. Read lengths of greater than 75 cycles are enabled with the addition of the antioxidant. As shown in the FIG. 9 inset, ascorbate also improved the % Q30. Additionally, ascorbate improved the % Align PhiX.

Similar results were observed with other concentrations of ascorbate (up to 20 mM), with varying concentrations of acetovanillone (up to 20 mM), and combinations of ascorbate and acetovanillone (data not shown).

In addition, the pH may be varied, and similar results may be obtained.

A number of embodiments have been described. Nevertheless, it will be understood that various modifications may be made. Accordingly, other embodiments are within the scope of the following claims.

What is claimed is:

1. A polynucleotide sequencing method comprising:
   (a) introducing a first chain extending enzyme and a mixture of blocked, labeled nucleotides to a flow cell comprising a site at which multiple template polynucleotide strands having the same nucleotide sequence are bound to a surface of the flow cell, wherein the first chain extending enzyme is configured to incorporate an appropriate one of the blocked, labeled nucleotides into copy polynucleotide strands, based on the sequence of the template strands to which the copy polynucleotide strands correspond;
   (b) washing unincorporated blocked, labeled nucleotides away from the flow cell;
   (c) introducing a composition comprising a mixture of blocked, unlabeled nucleotides to the flow cell during or after the washing away of the unincorporated blocked, labeled nucleotides from the flow cell, wherein a blocked, unlabeled nucleotide of the mixture of the blocked, unlabeled nucleotides is available for incorporation into the copy polynucleotide strands, based on a sequence of the template strands to which the copy polynucleotide strands correspond, provided that the previously incorporated nucleotide in the copy strand, if any, is not blocked; and
   (d) detecting the identity of the one blocked, labeled nucleotide incorporated into the copy strands, if any, while the mixture of blocked, unlabeled nucleotides is incubated with the flow cell;
   (e) removing a label and blocking moiety from any blocked, labeled nucleotide incorporated into the copy strands, and removing a blocking moiety from any blocked, unlabeled nucleotide incorporated into the copy strands; and
   (f) repeating steps (a)-(e),
   wherein the composition comprising the mixture of blocked unlabeled nucleotides has a pH of about 9 to about 9.5 and comprises a buffer, a detergent, magnesium sulfate, EDTA, and an antioxidant,
   wherein the error rate of detected nucleotide incorporation is less than 0.4% over 80 cycles when step (a) is performed for 7.5 seconds in each cycle,
   wherein the first chain extending enzyme comprises a recombinant DNA polymerase comprising an amino acid sequence that is at least 80% identical to a 9°N DNA polymerase amino acid sequence of SEQ ID NO. 1, wherein the recombinant DNA Polymerase comprises an amino acid substitution mutation at a position functionally equivalent to Tyr497 and at least on amino acid substitution mutation at a position functionally equivalent to Phe 152, Val278, Met329, Val471, Thr514, Leu631, or Glu734 in the 9°N DNA polymerase amino acid sequence.

2. The method of claim 1, wherein the composition comprising the mixture of blocked, unlabeled nucleotides is introduced to the flow cell after the washing away of the unincorporated blocked, labeled nucleotides from the flow cell.

3. The method of claim 1, wherein the washing the unincorporated blocked, labeled nucleotides away from the flow cell comprises the introducing the composition comprising the mixture of blocked, unlabeled nucleotides to the flow cell.

4. The method of claim 1, wherein the blocked, unlabeled nucleotide of the mixture of the blocked, unlabeled nucleotides is available for incorporation into the copy polynucleotide strands when the identity of the blocked, labeled nucleotide incorporated into the copy strands is being detected.

5. The method of claim 1, wherein detecting the identity of the blocked, labeled nucleotide incorporated into the copy strands comprises imaging the flow cell.

6. The method of claim 1, wherein the detecting the identity of the blocked, labeled nucleotide incorporated into the copy strands occurs over a period of time of 120 seconds or less.

7. The method of claim 1, wherein the detecting the identity of the blocked, labeled nucleotide incorporated into the copy strands occurs over a period of time of 10 seconds or more.

8. The method of claim 1, wherein the first chain extending enzyme and the mixture of blocked, labeled nucleotides are incubated with the flow cell for 15 seconds or less prior to the washing the unincorporated blocked, labeled nucleotides away from the flow cell.

9. The method of claim 1, wherein the first chain extending enzyme and the mixture of blocked, labeled nucleotides are incubated with the flow cell for 10 seconds or less prior to the washing the unincorporated blocked, labeled nucleotides away from the flow cell.

10. The method of claim 1, wherein the first chain extending enzyme and the mixture of blocked, labeled nucleotides are incubated with the flow cell for 7.5 seconds or less prior to the washing the unincorporated blocked, labeled nucleotides away from the flow cell.

11. The method of claim 1, wherein the composition comprising the mixture of blocked, unlabeled nucleotides comprises a second chain extending enzyme configured to incorporate an appropriate one of the blocked, unlabeled nucleotides into the copy polynucleotide strands, based on a sequence of the template strands to which the copy polynucleotide strands correspond, provided that the previously incorporated nucleotide in the copy strand, if any, is not blocked.

12. The method of claim 11, wherein the first chain extending enzyme and the second chain extending enzyme are the same enzymes.

13. The method of claim 1, wherein the buffer comprises Tris buffer, wherein the detergent comprises CHAPS, and wherein the antioxidant includes ascorbate, acetovanillone, or ascorbate and acetovanillone.

14. The method of claim 13, wherein the composition comprises ascorbate and acetovanillone.

15. The method of claim 14, wherein the composition comprises 3 to 20 mM ascorbate and 10 to 15 mM acetovanillone.

16. The method of claim 1, wherein the first chain extending enzyme comprises Pol812.

17. The method of claim 1, wherein the error rate of detected nucleotide incorporation is 0.35% or less over 80 cycles when step (a) is performed for 7.5 seconds in each cycle.

\* \* \* \* \*

SEQUENCE LISTING

```
<160> NUMBER OF SEQ ID NOS: 1

<210> SEQ ID NO 1
<211> LENGTH: 775
<212> TYPE: PRT
<213> ORGANISM: Artificial Sequence
<220> FEATURE:
<223> OTHER INFORMATION: Engineered Polymerase

<400> SEQUENCE: 1

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Asp Ile Glu Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
```

```
            305                 310                 315                 320
Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Thr Gly Asn Leu
                340                 345                 350

Val Glu Trp Phe Leu Leu Arg Lys Ala Tyr Lys Arg Asn Glu Leu Ala
                355                 360                 365

Pro Asn Lys Pro Asp Glu Arg Glu Leu Ala Arg Arg Gly Gly Tyr
                370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
                420                 425                 430

Val Ala Pro Glu Val Gly His Lys Phe Cys Lys Asp Phe Pro Gly Phe
                435                 440                 445

Ile Pro Ser Leu Leu Gly Asp Leu Leu Glu Glu Arg Gln Lys Ile Lys
                450                 455                 460

Arg Lys Met Lys Ala Thr Val Asp Pro Leu Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
                500                 505                 510

Val Thr Ala Trp Gly Arg Glu Tyr Ile Glu Met Val Ile Arg Glu Leu
                515                 520                 525

Glu Glu Lys Phe Gly Phe Lys Val Leu Tyr Ala Asp Thr Asp Gly Leu
                530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
                580                 585                 590

Lys Tyr Ala Val Ile Asp Glu Glu Gly Lys Ile Thr Thr Arg Gly Leu
                595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
                660                 665                 670

Tyr Lys Ala Thr Gly Pro His Val Ala Val Ala Lys Arg Leu Ala Ala
                675                 680                 685

Arg Gly Val Lys Ile Arg Pro Gly Thr Val Ile Ser Tyr Ile Val Leu
                690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735
```

```
Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
            755                 760                 765

Leu Lys Val Lys Gly Lys Lys
            770         775
```